US012635961B2

(12) United States Patent
Butani et al.

(10) Patent No.: US 12,635,961 B2
(45) Date of Patent: May 26, 2026

(54) SYSTEM AND METHOD FOR A GAMMA PROBE INCORPORATING SIMULTANEOUS ISOTOPE DETECTION

(71) Applicant: KUB TECHNOLOGIES, INC., Stratford, CT (US)

(72) Inventors: Vikram Butani, Fairfield, CT (US); Chester Lowe, Palm Springs, CA (US)

(73) Assignee: KUB TECHNOLOGIES, INC., Stratford, CT (US)

( * ) Notice: Subject to any disclaimer, the term of this patent is extended or adjusted under 35 U.S.C. 154(b) by 166 days.

(21) Appl. No.: 18/534,587

(22) Filed: Dec. 9, 2023

(65) Prior Publication Data

US 2025/0186008 A1 Jun. 12, 2025

(51) Int. Cl.
*A61B 6/42* (2024.01)
*A61B 6/00* (2006.01)
A61B 6/46 (2024.01)

(52) U.S. Cl.
CPC .............. *A61B 6/4258* (2013.01); *A61B 6/56* (2013.01); *A61B 6/461* (2013.01)

(58) Field of Classification Search
CPC .......... A61B 6/4258; A61B 6/56; A61B 6/461
See application file for complete search history.

(56) References Cited

U.S. PATENT DOCUMENTS

| | | | |
|---|---|---|---|
| 6,771,802 B1 * | 8/2004 | Patt ......................... | G01T 1/161 |
| | | | 382/128 |
| 11,039,803 B1 | 6/2021 | Butani et al. | |
| 2002/0117627 A1 * | 8/2002 | Jimbo ..................... | G01T 1/161 |
| | | | 600/436 |
| 2009/0177082 A1 * | 7/2009 | Baerwolff ................ | G01T 7/00 |
| | | | 600/436 |

(Continued)

OTHER PUBLICATIONS

United States Patent and Trademark Office, International Search Report, Application No. PCT/ US2024/059205, mailed Feb. 24, 2025, 2 pages.

(Continued)

*Primary Examiner* — Hugh Maupin
(74) *Attorney, Agent, or Firm* — Ziegler IP Law Group, LLC.

(57) ABSTRACT

It would be advantageous with the close quarters in breast procedure rooms to create a Gamma Probe system incorporating multi modalities, sensitivities, and multiple ranges for utilization in breast intervention procedures for the diagnosis and verification for breast cancer. Systems for specimen radiography assist radiologists and surgeons in the detection and classification of abnormal lesions in medical images gleaned from breast biopsies/lumpectomies and a Gamma Probe system with a sensor to detect radioactive, metallic/ magnet, or RFID waves to help locate a lump or abnormality which were placed by an Interventional Radiologist. Radio guided surgery (RGS) uses gamma probes to localize radioactive targets. The three common RGS radioisotopes: tech- (Continued)

Typical utilization of Detector Probe in tissue netium-99m (99mTc), indium-111 (111In), and iodine-125 (125I). The aspects of the disclosed embodiments pertain to a gamma probe that is able to simultaneously detect 2-3 isotopes automatically without actuating a physical switch.

10 Claims, 3 Drawing Sheets

(56) References Cited

U.S. PATENT DOCUMENTS

| | | | |
|---|---|---|---|
| 2013/0334429 A1* | 12/2013 | Fukuchi | G06T 7/0012 |
| | | | 250/363.03 |
| 2015/0238167 A1* | 8/2015 | Lall | A61B 6/037 |
| | | | 600/424 |
| 2017/0146668 A1* | 5/2017 | Evrard | G01T 1/20 |
| 2020/0147345 A1* | 5/2020 | Sinusas | A61B 5/4887 |
| 2020/0214571 A1 | 7/2020 | Bradbury et al. | |
| 2021/0000382 A1 | 1/2021 | Greene et al. | |
| 2022/0039683 A1* | 2/2022 | Harmer | A61B 5/742 |
| 2023/0161056 A1 | 5/2023 | Soluri et al. | |
| 2023/0346251 A1 | 11/2023 | Harmer et al. | |
| 2024/0164732 A1* | 5/2024 | Farsoni | G01T 1/161 |

OTHER PUBLICATIONS

United States Patent and Trademark Office, Written Opinion of the International Searching Authority, Application No. PCT/US2024/059205, mailed Feb. 24, 2025, 5 pages.

* cited by examiner

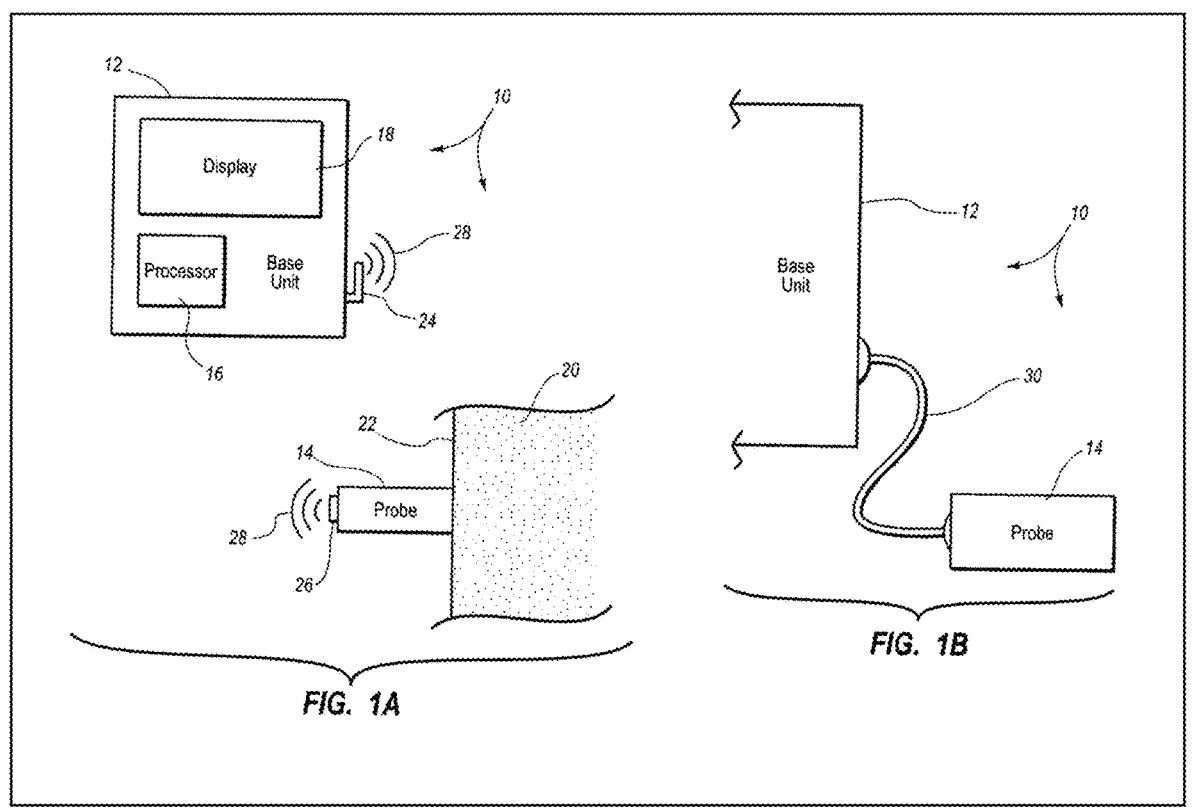
Fig. 1A and 1B - Block Diagram of Main Components

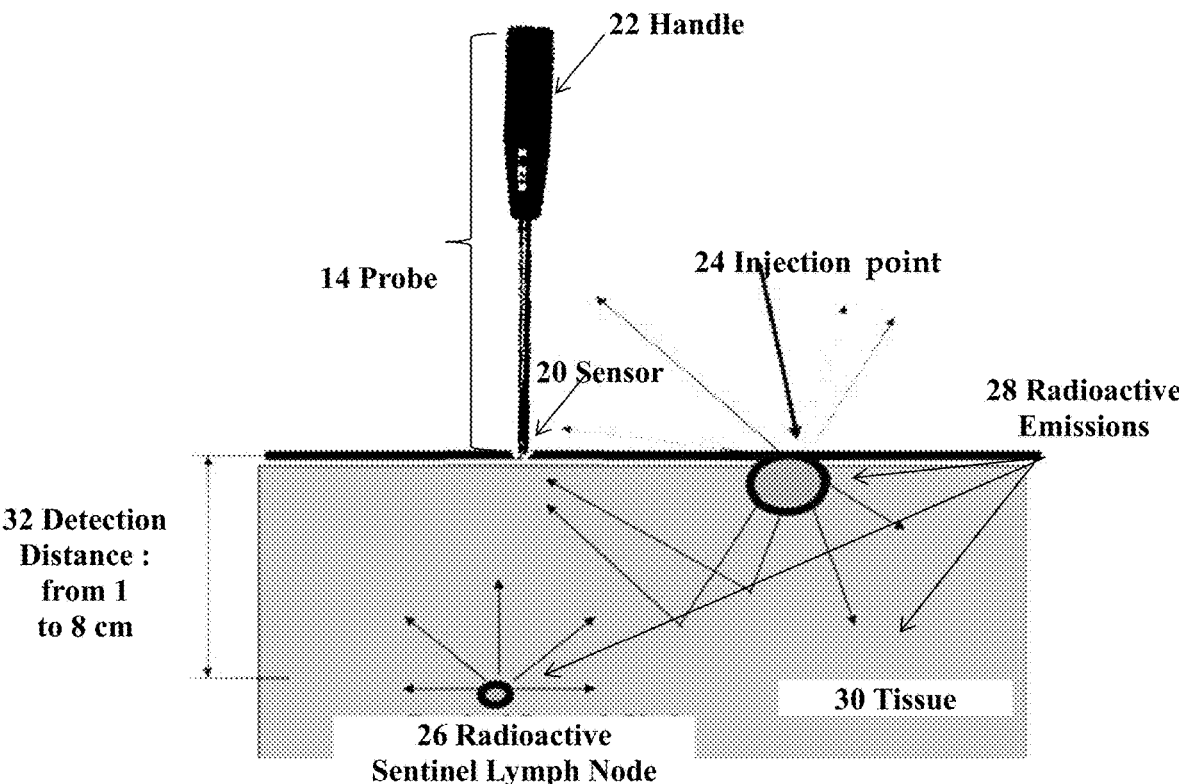
Fig. 2 – Typical utilization of Detector Probe in tissue

| Isotope | Photopeak keV | ADC Channel* |
|---------|---------------|--------------|
| Tc - 99m | 140 | 66 |
| Gd - 153 | 42 y 100 | 28 y 38 |
| Co - 57 | 122,1 | 60 |
| I-125 | 35.5 | 16 |
| F-18 | 511 | 117 |
| Ba-133 | 80 y 356 | 31 y 117 |
| Ga-68 | 511 | 117 |
| Na-22 | 511 | 117 |

Fig. 3 – Spectra of Different Isotopes

SYSTEM AND METHOD FOR A GAMMA PROBE INCORPORATING SIMULTANEOUS ISOTOPE DETECTION

CROSS-REFERENCE TO RELATED APPLICATIONS

This application is related to the following applications filed on 9 Dec. 2023, the disclosures of which are each, individually, incorporated herein by reference in their entireties: U.S. Ser. No. 18/534,584; U.S. Ser. No. 18/534,586; U.S. Ser. Nos. 18/534,588; 18/534,589; 18/534,590; 18/534, 591 and 18/534,592.

FIELD OF THE PRESENT DISCLOSURE

Radio guided surgery (RGS) uses gamma probes to localize radioactive targets. The three common RGS radio-isotopes: technetium-99m (99mTc), indium-111 (111In), and iodine-125 (125I). This aspects of the disclosed embodiments pertain to a gamma probe that is able to simultaneously detect 2-3 isotopes automatically without actuating a physical switch.

BACKGROUND

A gamma probe is a hand-held device for intraoperative use following interstitial injection of a radionuclide, to locate sentinel lymph nodes by their radioactivity. It is used primarily for sentinel lymph node mapping and parathyroid surgery.

The sentinel node experienced high growth during the last 10 years starting with melanoma sentinel node surgical search and breast cancer sentinel node staging; both are currently considered standards of care. New applications are being developed for parathyroid direct detection and intra-operative detection of cancerous tissue using tumor-seeking radiopharmaceuticals. Parathyroid detection is growing fast, while the intraoperative use of gamma probes for direct tumor detection is just emerging.

Numerous radionuclides have been utilized with the gamma detection probe in radio guided surgery. This includes, in alphabetical order, cobalt-57 ($^{57}$Co), F, gallium-67 ($^{67}$Ga), $^{111}$In, iodine-123 ($^{123}$I), $^{124}$I, $^{125}$I, $^{131}$I, $^{99m}$Tc, and thallium-201 ($^{201}$Tl)

In common practice, iodine-125 seeds are implanted into the patient's breast to demark the tumor site and Technetium-99m is injected into the breast to initial tracers of the lymphatic system to find the Sentinel Lymph Node or the primary Lymph Node filtering the patient's cancer.

It would be advantageous for the surgeon to be able to auditorily and graphically detect the location of the seed for surgical excision and detect which lymph nodes need to be removed.

Their respective ranges of energy are from 25-511 keV therefore a gamma detector with the proper detector and scintillator with corresponding smart electronics is necessary to 1$^{st}$ detect and then interpret the data received.

There are times when a physician may decide that a Gamma or other probe included in the present disclosure may be utilized to locate implanted seeds even for a mass that can be felt.

The sentinel node market experienced high growth in the early and mid 90's starting with melanoma sentinel node surgical search and breast cancer sentinel node staging; both are currently considered standards of care. Most surgeons propose node staging after a positive breast biopsy. New applications are being developed for parathyroid direct detection and intra-operative detection of cancerous tissue using tumor-seeking radiopharmaceuticals. Parathyroid detection is growing fast, while the intraoperative use of gamma or other probes for direct tumor detection is just emerging.

Currently there is believed to be no instruments that can concurrently and simultaneously track two to three isotopes.

SUMMARY

The Gamma Probe system of the disclosed embodiments consists of a console containing a computer and electronics, a video display screen, and a transducer/detector that is used to do the scanning. The probe is a small hand-held device that resembles a small pipe with a bigger cylindrical handle on one end, attached to the scanner by a cord or in this particular embodiment via Bluetooth. The detector of the probes of the present disclosure sense radioactivity, magnetic metal, or RFID (radio frequency identification) signals emitted by implanted seeds and sends a signal to the base unit on the strength of the detected signal creating a sound and a display on an analog screen informing the operator the locality of the seed from the tissues in the body. The principles are similar to a Geiger counter/sensor.

The sound and analog signal on a graph or dial is created based on the amplitude (loudness), frequency (pitch) and time it takes for the signal to be sensed from the area within the patient that is being examined to the Gamma or other probe (the device used to examine the patient), as well as the type of body structure and composition of body tissue through which the radioactivity, magnetism, or RFID travels.

This aspects of the disclosed embodiments utilize a Gadolinium Aluminum Gallium Garnet (GAGG) crystal with a Silicon Photomultiplier (SiPM) to first give the bandwidth detection of the above-named isotopes incorporated with the smart CPU incorporated into the analog to digital board enclosed into the handle. This data is then wirelessly transmitted via Bluetooth to the mated tablet which creates a corresponding strength sound and displays a strength signal on a bar graph. The incorporated software can simultaneously change scales by detecting the strength or wavelength of the detected isotope. The aspects of the disclosed embodiments visualizes the peak energies of each isotope to differentiate between them.

BRIEF DESCRIPTION OF THE DRAWINGS

To further clarify the above and other advantages and features of the aspects of a disclosed embodiments, a more particular description will be rendered by reference to specific embodiments thereof that are illustrated in the appended drawings. It is appreciated that these drawings depict only typical embodiments of the invention and are therefore not to be considered limiting of its scope. The invention will be described and explained with additional specificity and detail through the use of the accompanying drawings in which:

FIG. 1A is a simplified diagram of a Gamma Probe system configured in accordance with one example embodiment of the present disclosure;

FIG. 1B is a simplified view of a portion of FIG. 1A in accordance with an alternative example embodiment;

FIG. 2 is a display of Typical utilization of a Gamma Probe in tissue by the probe in FIG. 1A;

FIG. 3 is the table of the Spectra of Different Radioactive ISOTOPES;

DETAILED DESCRIPTION

Reference will now be made to figures wherein like structures will be provided with like reference designations. It is understood that the drawings are diagrammatic and schematic representations of exemplary embodiments of the invention, and are not limiting of the present invention nor are they necessarily drawn to scale.

FIGS. 1-3 depict various features of embodiments of the present disclosure, which embodiments are generally directed to a system for performing Gamma Probe—radioactive detection of the radioactive seeds in the body of a patient or other subject incorporated into a cabinet x-ray unit. Advantageously, the system to be described requires relatively low power levels in order to function, thereby enabling the system to take advantage of wireless technologies to un-tether the Gamma Probe from the base unit of the system. This, in turn, provides more flexibility for a clinician or other user of the system and simplifies the detection procedure.

Reference is first made to FIG. 1A, which shows a low power Gamma Probe system, generally designated at 10, configured in accordance with one example embodiment of the present invention. As shown, the Gamma Probe system ("system") 10 generally includes a base unit 12 and Gamma Probe 14. The base unit 12 as pictured here includes a processor 16 for performing processing functions on emission data retrieved by the probe 14 during a Sentinel Node or radioactive localization procedure.

FIG. 1A shows the probe 14 placed adjacent a surface 22 of a body 20 of a patient or other subject. Though understood to be used in applications such as that shown here in FIG. 1A, it is also appreciated that embodiments of the present disclosure may be modified for use with probes having other shapes and configurations, including probes configured for penetration into an orifice of the patient, for instance.

The base unit 12 further includes a display 18. Emission data processed by the processor 16 of the base unit 12 are represented as an audio sound and an analog image on the display 18. The image is continually refreshed during operation of the system 10. Note that, for clarity, only selected features of the base unit 12, probe 14, and the system 10 are described herein in detail. Indeed, it is appreciated that the system 10 and its individual components can include additional features and components, though not disclosed herein, while still preserving the principles of the aspects of the disclosed embodiments. Note also that the base unit 12 can be one of any number devices, including a dedicated Gamma Probe device, a desktop or laptop computer, etc.

In the presently depicted embodiment, the system 10 implements wireless technology, wherein the base unit 12 and the probe 14 are in two-way, wireless communication with one another. To that end, the base unit 12 includes a base antenna 24 that wireless communicates with a probe antenna 26 included with the probe 14.

Wireless signals 28, representing electromagnetic communication such as RF signals between the base unit 12 and the probe 14, are also shown. In this way, sonographic data detected by the probe 14 can be wirelessly transmitted by the probe antenna 26 to the base unit 12 via the base antenna 24 for processing by the processor 16. Note that one or more of a variety of wireless data transfer protocols, including Wireless USB, IEEE 802.x, BLUE TOOTH, WIMAX, etc., may be employed for such data transfer as described herein.

FIG. 1B represents another possible embodiment, wherein the base unit 12 of the low Gamma Probe system 10 is communicatively coupled with the probe 14 not wirelessly, but via a cable 30. As such, it is appreciated that the Gamma Probe system as described herein may be employed with a wireless, non-wireless, or even hybrid wireless/cabled communication link between the base unit and the probe.

Reference is now made to FIG. 2, which depicts various details regarding the probe 14 of the system 10 shown in FIG. 1A. As depicted, the probe 14 according to the present embodiment is a wireless probe and includes a probe housing that acts as a covering for various internal components of the probe.

A sensor head 20 with a handle 22 is included in the probe 14 and houses the array of sensors that act as transducers to enable detection of the emissions 28 of an object within the body of the patient 30 to be detected within the distance 32 of 1-8 cm from the skin surface during seed localization procedures. In one instance, Sentinel Node Localization, Technetium 99, a radioactive isotope, is injected at point 24 and the probe is scanned to detect the emissions 28 of the Technetium 99 or other radionuclide as it courses through the patient's body.

Thus, it is appreciated that the probe 14 as shown in FIG. 2 can be desirably included within the sterile field of a patient undergoing a procedure in preparation for a lumpectomy for instance. Note that the particular design of the probe 14 as shown in FIG. 2, together with the specified location for the various components thereof both internal and external can be varied such that the size, look, and configuration of the probe may be modified from what is explicitly shown as displayed in FIG. 2.

The resulting signals as received by the base unit are processed by the processor 16 to form an audio signal as well as an analog signal display image of the scanned object 26 FIG. 2 detecting the emissions 28. All of the above Gamma Probe components, in this embodiment, are able to discern different radioactive isotope spectra as show in FIG. 3 with 100 incorporating unit 10, FIG. 1A and displaying the emission signal as previously mentioned in FIG. 1A—18 in components FIG. 3—101, 102, 103, 104.

The present invention may be embodied in other specific forms without departing from its spirit or essential characteristics. The described embodiments are to be considered in all respects only as illustrative, not restrictive. All changes that come within the meaning and range of equivalency of the claims are to be embraced within their scope.

What is claimed is:

1. A Gamma Probe device, comprising:
    a head portion including a sensor
    a base unit including an image processor and a display;
    a Gamma Probe configured to be connected to the base unit, the probe including:
        a plurality of receiver modules configured to sense magnetic metal, RFID, and simultaneously detect two or three different radioactive spectra from Tc-99m, Gd-153; Co-57, I-125, F-18, Ba-133, Ga-68, and Na-22 by visualizing the peak energy of each isotope;
        a processing unit that controls the receiver modules and an analog-to-digital converter, the receiver modules causing the Gamma Probe to receive data until a target object is scanned; and
        an interface for enabling a digital signal to be transferred from the Gamma Probe to an image processor of the base unit.

2. The Gamma Probe device as defined in claim 1, wherein the probe further comprises a sensor that actuates to create analog signals which are amplified by the base unit to create an audible sound.

3. The Gamma Probe device as defined in claim 1, wherein the probe includes a battery for providing power to components of the probe.

4. The Gamma Probe device as defined in claim 3, wherein the interface is a wireless interface, and wherein the base unit includes a wireless interface.

5. The Gamma Probe device as defined in claim 4, wherein the wireless interface of the probe and the base unit communicate via a wireless data transfer protocol.

6. The Gamma Probe device as defined in claim 1, wherein the interface includes a cable interface between the probe and the base unit.

7. The Gamma Probe device as defined in claim 1, wherein the sensor produces a differential output of amplified analog signals.

8. The Gamma Probe device as defined in claim 1, wherein the base unit is a computer.

9. The Gamma Probe device as defined in claim 1, wherein the sensor will attenuate to a radioactive seed or radioisotope.

10. The Gamma Probe device of claim 1, wherein the Gamma Probe comprises a Gadolinium Aluminum Gallium Garnet (GAGG) crystal with a Silicon Photomultiplier (SiPM) configured to provide a bandwidth detection for discerning the different radioactive spectra.

\* \* \* \* \*